(12) United States Patent
Auffinger et al.

(10) Patent No.: US 10,345,220 B1
(45) Date of Patent: Jul. 9, 2019

(54) FLUID TESTING SYSTEMS AND METHODS

(71) Applicant: THE BOEING COMPANY, Chicago, IL (US)

(72) Inventors: Sean Auffinger, Ladson, SC (US); Brandon David Booth, Mt. Pleasant, SC (US)

(73) Assignee: The Boeing Company, Chicago, IL (US)

( * ) Notice: Subject to any disclaimer, the term of this patent is extended or adjusted under 35 U.S.C. 154(b) by 184 days.

(21) Appl. No.: 15/233,490

(22) Filed: Aug. 10, 2016

(51) Int. Cl.
*G01N 17/00* (2006.01)
*G01D 11/24* (2006.01)
*G01N 35/00* (2006.01)

(52) U.S. Cl.
CPC .......... *G01N 17/002* (2013.01); *G01D 11/24* (2013.01); *G01N 2035/00306* (2013.01)

(58) Field of Classification Search
CPC ....... G01N 17/002; G01N 2035/00178; G01N 2035/00306; G01D 11/24; G01D 18/00; G01D 21/00; G01M 13/00; G01M 13/005
USPC .................................. 73/118.01, 168, 865.6
See application file for complete search history.

(56) References Cited

U.S. PATENT DOCUMENTS

| | | | | | |
|---|---|---|---|---|---|
| 3,210,986 A | * | 10/1965 | Hart | ........................ | G01N 3/18 374/50 |
| 3,580,050 A | * | 5/1971 | Waldron | .................. | G01N 3/10 73/37 |
| 3,911,735 A | * | 10/1975 | Di Crispino | ............. | G01N 3/12 73/37 |
| 4,381,663 A | * | 5/1983 | Swanson | .................. | G01N 3/36 73/168 |

* cited by examiner

*Primary Examiner* — Benjamin R Schmitt
(74) *Attorney, Agent, or Firm* — Jospeh M. Butscher; The Small Patent Law Group, LLC

(57) ABSTRACT

A fluid testing system includes a component test housing that includes a plurality of walls connected to a base and a cover. A test chamber is defined between the plurality of walls, the base, and the cover. The test chamber is configured to receive a sample component to be subjected to a fluid test. Fluid inlet ports are formed through the component test housing. The Fluid inlet ports are configured to allow test fluid to flow into the test chamber from at least two different directions.

19 Claims, 6 Drawing Sheets

FLUID TESTING SYSTEMS AND METHODS

FIELD OF THE DISCLOSURE

Embodiments of the present disclosure generally relate to fluid testing systems and methods.

BACKGROUND OF THE DISCLOSURE

Various components are subjected to fluid tests to determine how such components will react to various environmental conditions. For example, fasteners that are used to secure panels together may be subjected to fluid slosh tests to determine how fluids, such as liquids, affect the fasteners.

A typical fluid slosh test system includes a testing tank that is coupled to an axle. The tank is configured to receive and retain one or more components therein. Fluid, such as water, is retained within the tank. The tank is then rotated about the axle to so that the water sloshes back and forth within the tank, thereby flowing into and around the components that are being tested.

Typically, the testing tank is a costly, large metal tank (for example, capable of retaining one hundred or more gallons of liquid). Further, the actual fluid test is time-consuming. In particular, a typical fluid slosh test involves the testing tank rocking back and forth for a month or longer.

Also, the conditions inside the testing tank may or may not be comparable to actual environmental conditions that a component experiences. For example, the single axis of rotation of the testing tank is only able to simulate fluid slosh test with respect to the single axis, which may not accurately simulate actual environmental conditions.

SUMMARY OF THE DISCLOSURE

A need exists for a system and method for efficiently and effectively performing a fluid test with respect to one or more components. A need exists for a cost effective and adaptable fluid test that more accurately simulates actual environmental conditions.

With those needs in mind, certain embodiments of the present disclosure provide a fluid testing system that includes a component test housing including a plurality of walls connected to a base and a cover. A test chamber is defined between the plurality of walls, the base, and the cover. The test chamber is configured to receive a sample component to be subjected to a fluid test. A plurality of fluid inlet ports are formed through the component test housing. The plurality of fluid inlet ports are configured to allow test fluid to flow into the test chamber from at least two different directions.

In at least one embodiment, a test panel is configured to retain the sample component. The base may include a recessed area. The test panel is removably secured to the recessed area.

The fluid testing system may also include at least one fluid reservoir in fluid communication with the test chamber. Each of the plurality of fluid inlet ports may be coupled to the fluid reservoir(s) through one or more conduits.

One or more valves may be disposed within the conduit(s). The valve(s) are configured to be selectively moved between open and closed positions to vary flow of the test fluid into the test chamber through the plurality of fluid inlet ports.

At least one pump may be coupled to the conduit(s). The pump(s) is configured to circulate the test fluid between the test chamber and the fluid reservoir(s). The pump(s) may be operated to variably control a flow rate of the test fluid into the test chamber.

In at least one embodiment, the fluid testing system includes at least two fluid reservoirs. In at least one embodiment, a first fluid reservoir retains a first test fluid, and a second fluid reservoir retains a second test fluid that differs from the first test fluid.

The fluid testing system may include at least one temperature control device that is configured to control a temperature of the test fluid.

In at least one embodiment, the component test housing is stationary during the fluid test.

Certain embodiments of the present disclosure provide a fluid testing method that includes receiving a sample component to be subjected to a fluid test within a test chamber of a component test housing that includes a plurality of walls connected to a base and a cover. The test chamber is defined between the plurality of walls, the base, and the cover. The method also includes selectively flowing test fluid into the test chamber from at least two different directions through a plurality of fluid inlet ports formed through the component test housing.

DETAILED DESCRIPTION OF THE DISCLOSURE

Figure 1:
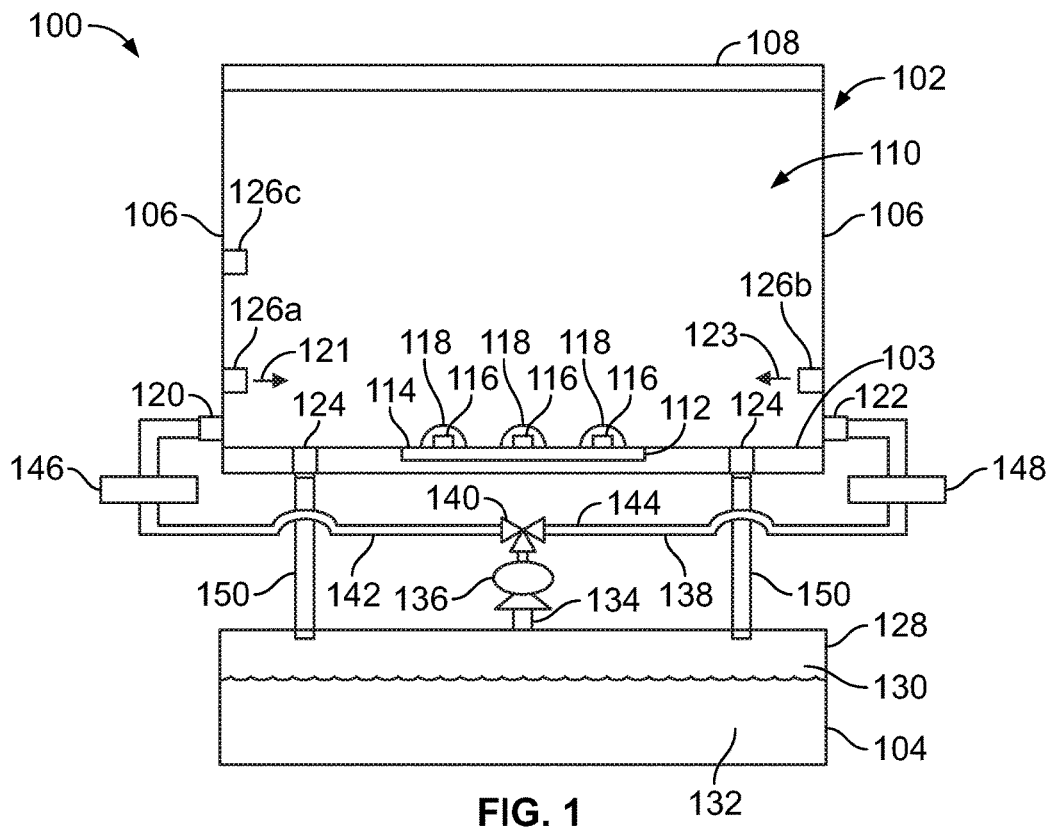
FIG. 1 illustrates a schematic diagram of a fluid testing system, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a fluid testing system and method that includes a component test housing that defines a test chamber. Components to be tested are mounted in the test chamber. In at least one embodiment, a mounting panel may receive and retain the components. The mounting panel may be removably secured to a portion of the component test housing that defines the test chamber. The component test housing includes multiple fluid inlet ports that allow fluid to flow into the test chamber from multiple locations. Testing fluids (such as water, fuel, oil, or other such liquids) flow through the fluid inlet ports and flow into and around the components within the test chamber, such as to simulate fluid sloshing in a tank.

In at least one embodiment, a component to be tested (for example, a component sample) is mounted in the test chamber. Test fluid is pumped through the multiple fluid inlet ports. Each fluid inlet port may be selectively opened or closed. Various parameters for each fluid inlet port may be controlled, such as fluid temperature, fluid flow rate, fluid type, and duration of fluid flow. One or more sensors (such as pressure sensors, flow rate sensors, temperature sensors, and/or the like) may be mounted in the test chamber to detect various conditions within the test chamber. In at least one embodiment, the component test housing may be formed of a transparent material (such as glass, transparent plastic, or the like) in order to allow for visual observation of the sample during the fluid test.

Certain embodiments of the present disclosure provide a fluid testing system that includes a test fluid reservoir, a component test housing defining a test chamber, and a pump. The test fluid reservoir is in fluid communication with the test chamber. A test component (for example, a component sample) is secured within the test chamber. In at least one embodiment, the test component is a seal cap, such as a sealant capped bolt head. The pump is configured to pump test fluid from the test fluid reservoir into the test chamber at predetermined flow rates and/or at predetermined intervals.

Embodiments of the present disclosure provide fluid testing systems and methods that are more compact than known testing systems. Further, it has been found that embodiments of the present disclosure provide quicker and more efficient fluid tests than known testing systems and methods.

FIG. 1 illustrates a schematic diagram of a fluid testing system 100, according to an embodiment of the present disclosure. The fluid testing system 100 includes a component test housing 102 that is in fluid communication with a test fluid reservoir 104.

The component test housing 102 includes a base 103 connected to a plurality of walls 106 that connect to a cover 108. The cover 108 may be removably coupled to the walls 106. For example, the cover 108 may be a lid that is configured to be selectively removed from and positioned over the walls 106. In at least one other embodiment, the cover 108 may be coupled to one or more of the walls 106 through one or more hinges. A test chamber 110 is defined between the base 103, the walls 106, and the cover 108.

Although the exemplary embodiment illustrates the component test housing 102 having a square or rectangular shape, it should be realized that the component test housing 102 may have any suitable shape, and the shape shown in FIG. 1 is one example.

The component test housing 102 may be formed from a transparent material, such as glass, plexiglass, transparent plastics, and/or the like. Alternatively, the component test housing 102 may be formed of opaque materials, such as various metals.

During a fluid test, the component test housing 102 is stationary in that it is not configured to rotate about an axis. During a fluid test, the component test housing 102 remains in a fixed position. In this manner, the fluid test may be more cost effective as additional axles, motors, and/or the like are not required to rotate the component test housing 102.

The base 103 includes a recessed area 112 that removably retains a test panel 114. The test panel 114 includes one or more component retainers 116 (such as bolts, studs, clasps, barbs, and/or the like) that receive and retain one or more sample components 118. The sample components 118 are components that are to be subjected to a fluid test. The sample components 118 may be seal caps, such as sealant capped bolt heads. Optionally, the sample components 118 may be various other components that are to be subjected to a fluid test, such as fasteners, beams, panels, plates, and/or the like. In at least one other embodiment, the fluid testing system 100 may not include the test panel 114. Instead, the sample components 118 may be mounted to one or more structures within the test chamber 110 (such as component retainers 116 upwardly extending from the base 103). Optionally, the sample components 118 may merely be supported by an upper surface of the base 103.

Multiple fluid inlet ports 120 and 122 are formed through the component test housing 102. The fluid inlet ports 120 and 122 provide passages within the component test housing 102 through which fluid may pass. As shown, the component test housing 102 includes two fluid inlet ports 120 and 122 formed through the walls 106. Optionally, the component test housing 102 may include more than two fluid inlet ports. Further, the fluid inlet ports may be formed through various other portions of the component test housing 102, such as the cover 108 and/or the base 103.

As shown in FIG. 1, the fluid inlet ports 120 and 122 are formed through opposite walls (such as opposite end walls or opposite side walls). As such, the fluid inlet ports 120 and 122 provide fluid paths into the test chamber 110 from opposite directions 121 and 123. Optionally, at least one of the fluid inlet ports 120 and 122 may be formed through a different wall 106, the cover 108, or the base 103.

One or more fluid outlet ports 124 are formed through the base 103 and/or the walls 106. The fluid outlet ports 124 provide drains through which test fluid drains out of the test chamber 110.

In at least one embodiment, one or more sensors 126a, 126b, and 126c are located within the test chamber 110. The sensors 126a-c are configured to sense one or more parameters within the test chamber 110. In at least one embodiment, the sensor 126a is or includes a thermometer that is configured to detect fluid or gas temperature within the test chamber 110. In at least one embodiment, the sensor 126b is a fluid flow rate sensor that is configured to detect a velocity of fluid flowing within the test chamber 110. In at least one embodiment, the sensor 126c is a pressure sensor (for example, a barometer) that is configured to detect a pressure of gas and/or liquid within the test chamber 110. The sensors 126a-c are in communication with a computing device, a processor(s), and/or the like (such as through one or more wired or wireless connections) that receives sensed outputs from the sensors 126a-c. Additional temperature, flow, and pressure sensors may also be used, if desired. Alternatively, the test chamber 110 may not include all of the sensors 126a-c.

The fluid reservoir 104 includes a retaining body 128 that defines a retaining chamber 130 that retains test fluid 132. In at least one embodiment, the test fluid 132 is water. In at least one other embodiment, the test fluid 132 is fuel, oil, or various other liquids.

A fluid outlet conduit 134 (such as a pipe, hose, tube, or the like) is in fluid communication with the retaining chamber 130. A pump 136 is operatively coupled to the fluid outlet conduit 134. The fluid outlet conduit 134 couples to a branching conduit 138 (such as a pipe, hose, tube, or the like) through a valve 140. In this embodiment, the valve 140 is a three way valve that is selectively operable to allow fluid to pass into first and second segments 142 and 144 of the branching conduit 138, or prevent passage of the fluid into the first and/or second segments 142 and 144. The valve 140 may be a manual valve or an automatic valve.

The first segment 142 of the branching conduit 138 couples to and is in fluid communication with the fluid inlet port 120. The second segment 144 of the branching conduit 138 couples to and is in fluid communication with the fluid inlet port 122.

A pair of temperature control devices 146 and 148 are disposed within the first and segments 142 and 144, respectively. The temperature control devices 146 and 148 are configured to control a temperature of the fluid passing into the test chamber 110. The temperature control devices 146 and 148 may be heaters, heat exchangers, refrigerant coils, chillers, and/or the like. Alternatively, the fluid testing system 100 may not include the temperature control device 146 and 148.

In operation, the pump 136 pumps the test fluid 132 from the fluid reservoir 104 into the fluid outlet conduit 134. The test fluid 132 is pumped toward and into the valve 140. In a first position, the valve 140 allows the test fluid 132 to flow into both the first and second segments 142 and 144 of the branching conduit 138, thereby allowing the test fluid 132 to flow into the test chamber 110 from the fluid inlet port 120 and 122 and flow into and around the sample components 118. In a second position, the valve 140 closes the first segment 142 so that the test fluid 132 only flows into the second segment 144, such that the test fluid 132 flows into the test chamber 110 only from a first direction out of the fluid inlet port 122. In a third position, the valve 140 closes the second segment 144 so that the test fluid 132 only flows into the first segment 142, such that the test fluid flows into the test chamber 110 only from a second direction out of the fluid inlet port 120. In a fourth position, the valve 140 closes both the first and second segments 142 and 144, thereby preventing the test fluid 132 from flowing into the test chamber 110. In this manner, the valve 140 is engageable to provide selective fluid flow into the test chamber 110 from one or more desired directions, thereby allowing for a variable flow direction fluid test.

As the test fluid 132 flows through the segments 142 and 144, the temperature control devices 146 and 148 control a temperature of the test fluid 132 before the test fluid 132 enters the test chamber 110. For example, the temperature control devices 146 and 148 may heat or cool the test fluid 132. In this manner, the fluid testing system 100 is configured to provide a variable temperature fluid test.

Additionally, the rate of fluid flow into the test chamber 110 may be varied by the pump 136. For example, the pump 136 may be operated at variable rates to vary the flow of the test fluid 132 into the test chamber 110. As such, the fluid testing system 100 is configured to provide a variable flow rate fluid test.

Test fluid 132 within the test chamber 110 drains out of the component test housing 102 through the fluid outlet port(s) 124 into return conduit(s) 150 (such as a pipe, hose, tube, or the like), which are in fluid communication with the retaining chamber 130 of the fluid reservoir 104. Thus, the test fluid 132 is returned back to the fluid reservoir 104 from the test chamber 110. As the pump 136 continues to operate, the test fluid 132 circulates between the fluid reservoir 104 and the test chamber 110.

As noted, the component test housing 102 is stationary (for example, fixed in position) during the fluid test. Instead of rotating the component test housing 102 back and forth with respect to a single axis of rotation to slosh fluid within the test chamber 110, the multiple fluid inlet ports 120 and 122 provide fluid flow from multiple directions, which may be selectively controlled, as noted above. Instead of rotating the component test housing 102, the fluid inlet ports 120 and 122 are used to create sloshing forces in the test chamber 110. The velocity of fluid passing out of the fluid inlet ports 120 and 122 is easier to vary, as compared to fluid within a rotating housing. Further, the component test housing 102 takes is space-efficient, in that the velocity of fluid flow does not depend upon the size and motion of a rotating housing.

Further, the temperature control device 146 and 148 may be operated to vary the temperature of the test fluid 132. Moreover, the flow of the test fluid into and out of the test chamber 110 may be controlled through selective operation of the pump 136. As such, the fluid testing system 100 allows for various parameters (such as flow direction, flow rate, and fluid temperature) to be selectively controlled. In this manner, the fluid test may be adjusted as desired to provide a test environment that better simulates an actual environment in which a component is used.

Figure 2:
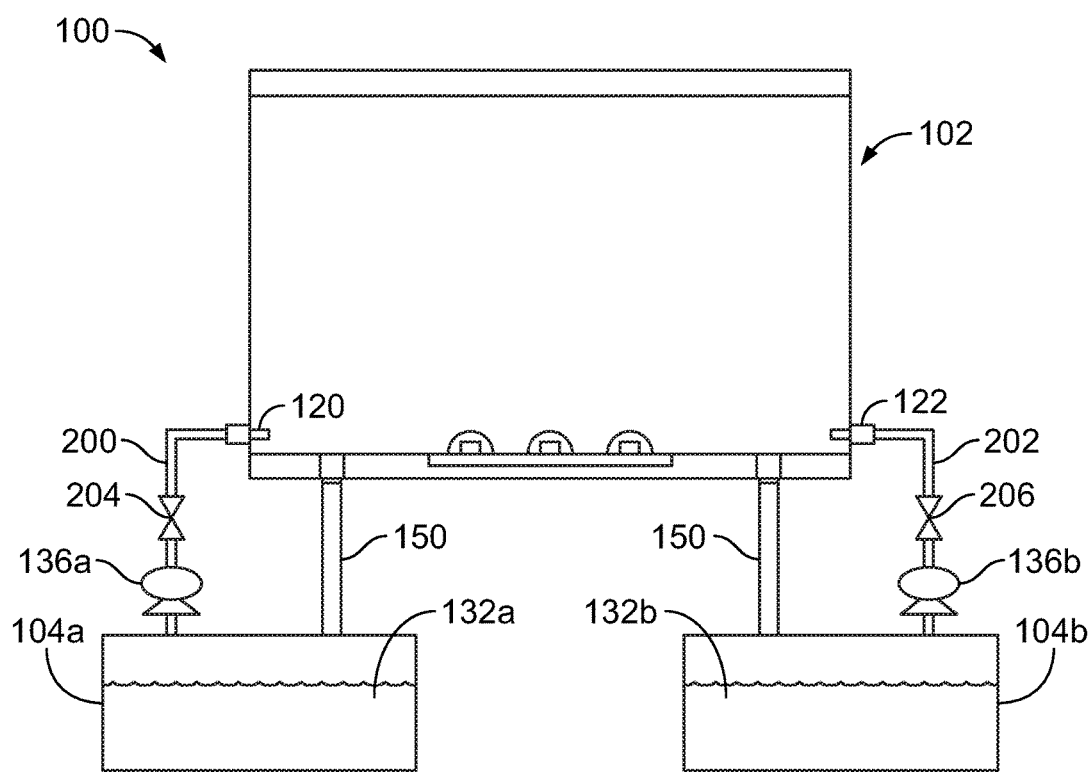
FIG. 2 illustrates a schematic diagram of a fluid testing system, according to an embodiment of the present disclosure.

FIG. 2 illustrates a schematic diagram of the fluid testing system 100, according to an embodiment of the present disclosure. The embodiment shown in FIG. 2 is similar to that shown in FIG. 1, except that separate and distinct fluid reservoirs 104a and 104b may be in fluid communication with the fluid inlet ports 120 and 122, respectively, through separate and distinct fluid conduits 200 and 202, respectively. Each fluid reservoir 104a and 104b retains a respective test fluid 132 and 132b. Each fluid reservoir 104a and 104b may contain the same or different test fluid 132a and 132b. Optionally, each of the fluid conduits 200 and 202 may be in fluid communication with a single, common fluid reservoir, such as the fluid reservoir 104 shown in FIG. 1.

A valve 204 is disposed within the fluid conduit 200, while a valve 206 is disposed within the fluid conduit 202. In open positions, the valves 204 and 206 allow fluid to flow therethrough. In closed positions, the valves 204 and 206 prevent flow therethrough. Further, a pump 136a may be coupled to the fluid conduit 200, while a separate and distinct pump 136b may be coupled to the fluid conduit 202.

Figure 3:
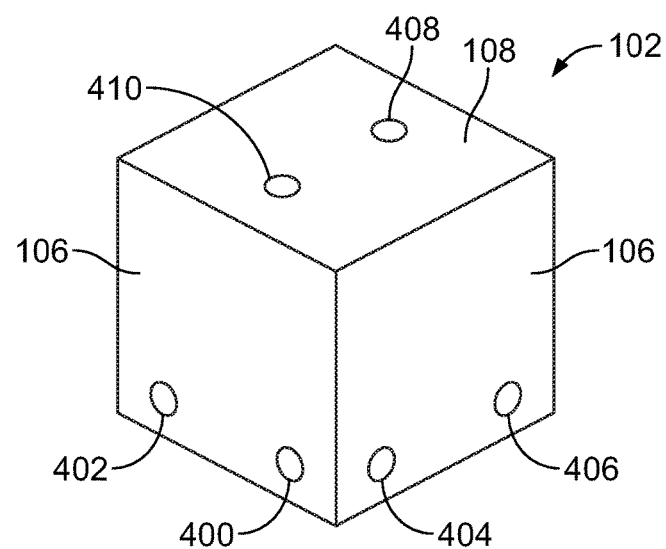
FIG. 3 illustrates a perspective top view of a component test housing, according to an embodiment of the present disclosure.

FIG. 3 illustrates a perspective top view of a component test housing 102, according to an embodiment of the present disclosure. As shown, each wall 106 of the component test housing 104 includes multiple fluid inlet ports 400, 402, 404, and/or 406. Further, the cover 108 includes multiple fluid inlet ports 408 and 410. Each fluid inlet port 400-410 is configured to be coupled to a fluid inlet conduit that is in communication with at least one fluid reservoir, such as those shown and described with respect to FIGS. 1-3. Each wall 106 and the cover 108 may include more or less fluid inlet ports than shown. Further, the base (hidden from view in FIG. 4) may include one or more fluid inlet ports.

Figure 4:
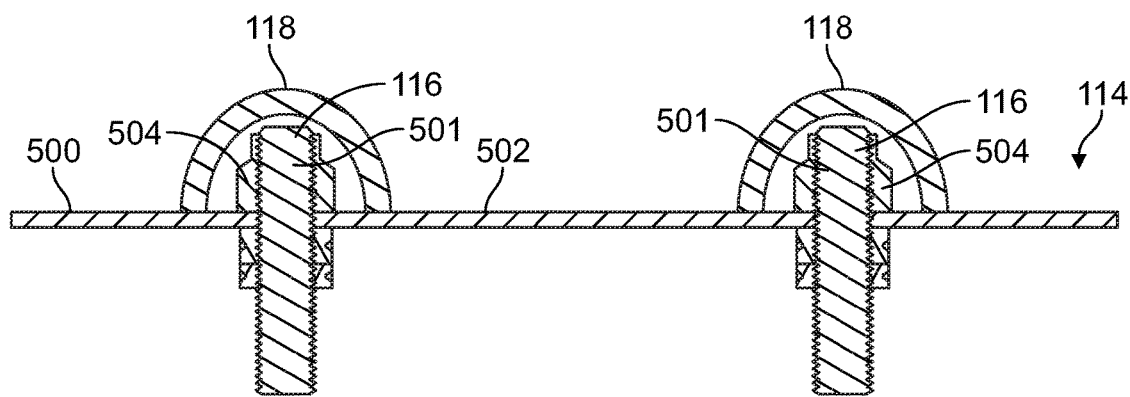
FIG. 4 illustrates a transverse cross-sectional view of a test panel, according to an embodiment of the present disclosure.

FIG. 4 illustrates a transverse cross-sectional view of the test panel 114, according to an embodiment of the present disclosure. Referring to FIGS. 1 and 4, the test panel 114 includes a planar sheet 500 that is configured to be received and retained within the recessed area 112 formed in the base 103 of the component test housing 102. The recessed area 112 is sized and shaped to reciprocally conform around the sheet 500. The retainers 116 may be bolts, screws, or other such fasteners that are received and retained by reciprocal features formed in the base 103 to securely fix the test panel 114 within the recessed area 112. A portion 501 of each retainer 116 extends above an upper surface 502 of the sheet 500. A mount 504 may be secured around the portion 501. The sample components 118 securely fix to the test panel 114 via the portions 501 and/or the mounts 504. The test panel 114 may be configured to retain more or less sample components 118 than shown. Optionally, the sample components 118 may be secured to the test panel 114 through adhesives.

In at least one embodiment, the sample components 118 are pre-cured polysulfide seal caps. The pre-cured seal caps may be filled with uncured sealant and placed over the portions 501 of the retainers 116 and/or the mounts 504.

Figure 5:
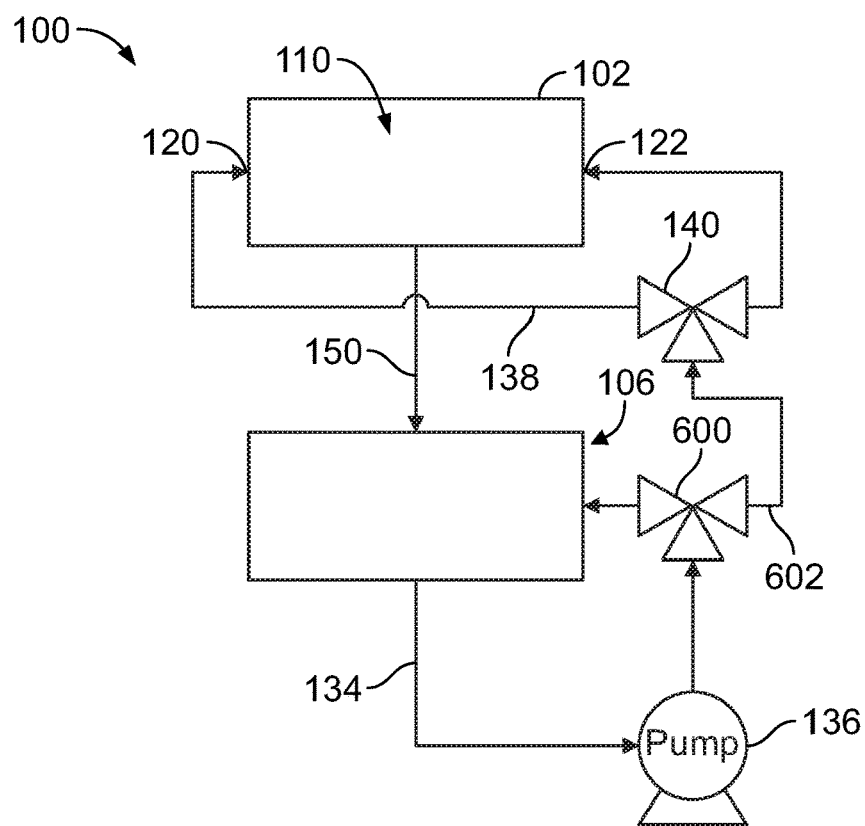
FIG. 5 illustrates a schematic diagram of a fluid testing system, according to an embodiment of the present disclosure.

FIG. 5 illustrates a schematic diagram of the fluid testing system 100, according to an embodiment of the present disclosure. In this embodiment, a three way valve 600 is coupled to the conduit 134 (such as through the pump 136) and a first branching conduit 602 that connects to the fluid reservoir 104 and the three way valve 140. In turn, the valve 140 is coupled to the branching conduit 138, as described above with respect to FIG. 1.

The valve 140 may be selectively moved between multiple positions, as described above, to selectively control the direction of test fluid into the test chamber 110 through the fluid inlet ports 120 and 122. Similarly, the valve 600 may be selectively moved between multiple positions. In a first position, the valve 600 is closed to the valve 140, but open to the fluid reservoir 104, thereby allowing the pump 136 to continually circulate the test fluid into and out of the fluid reservoir (such as to mix the test fluid). In a second position, the valve 600 is open to both the valve 140 and the fluid reservoir 104. In a third position, the valve 600 is closed to the fluid reservoir 104 and open to the valve 140.

Figure 6:
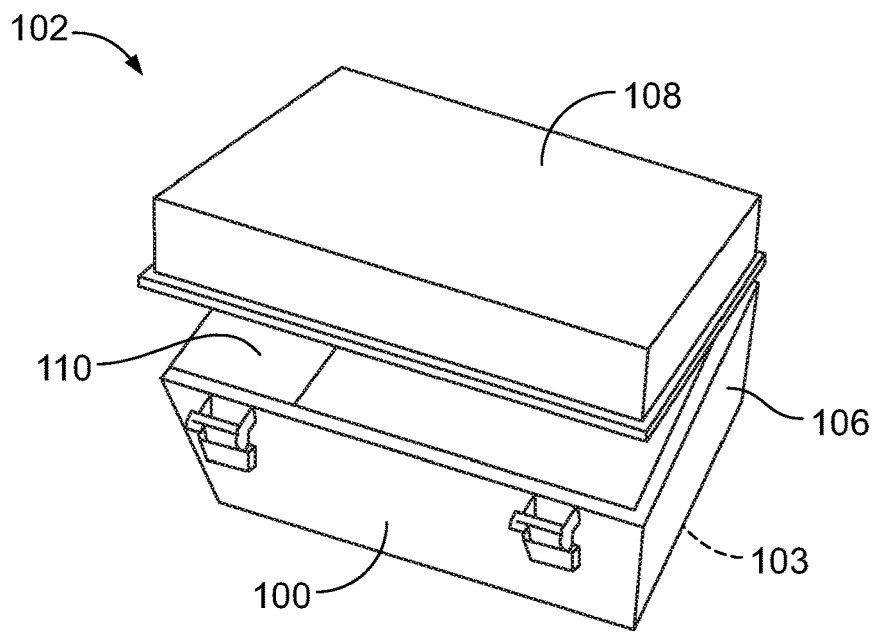
FIG. 6 illustrates a perspective top view of a component test housing, according to an embodiment of the present disclosure.

FIG. 6 illustrates a perspective top view of the component test housing 102, according to an embodiment of the present disclosure. As shown, the cover 108 may be pivotally secured to one of the walls 106. As such, the cover 108 may be opened to allow sample components to be positioned within (and removed from) the test chamber 110.

Figure 7:
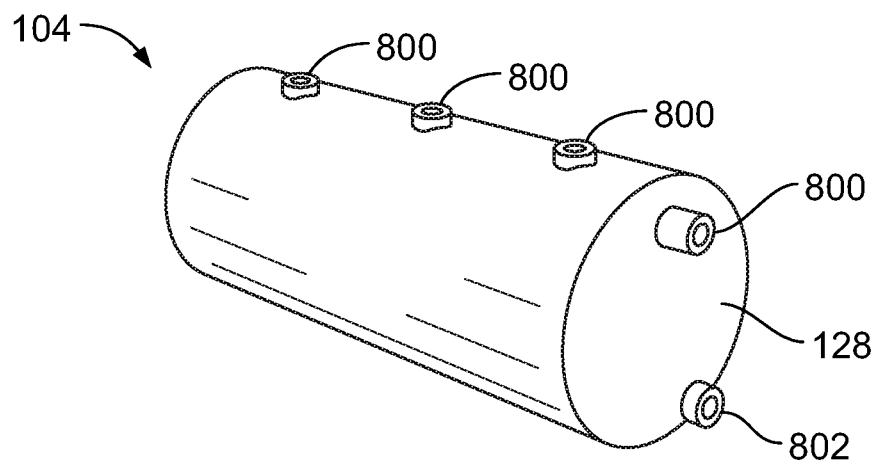
FIG. 7 illustrates a perspective top view of a fluid reservoir, according to an embodiment of the present disclosure.

FIG. 7 illustrates a perspective top view of the fluid reservoir 104, according to an embodiment of the present disclosure. As shown, the fluid reservoir 104 may be a tubular tank having a plurality of ports 800 and 802 which may be inlet or outlet ports that couple to conduits.

Figure 8:
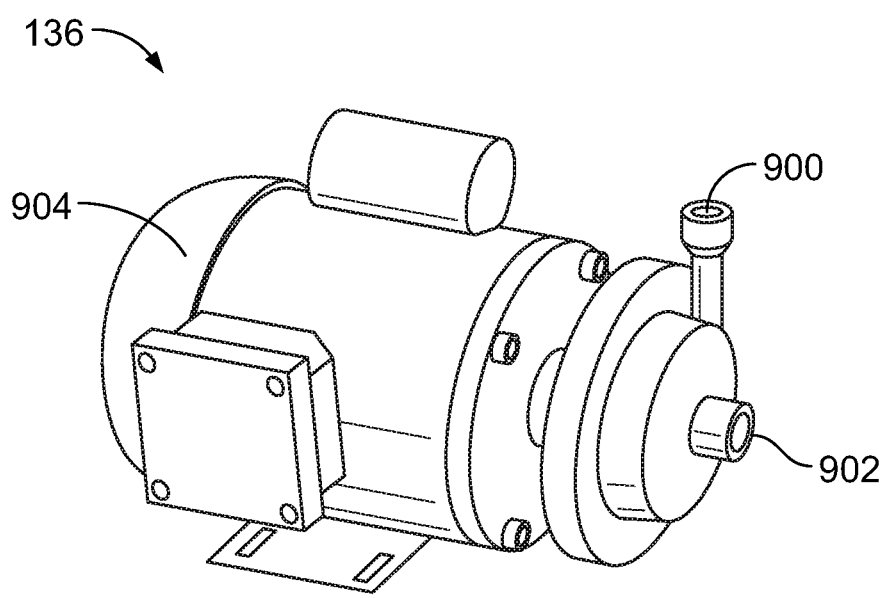
FIG. 8 illustrates a perspective lateral view of a pump, according to an embodiment of the present disclosure.

FIG. 8 illustrates a perspective lateral view of the pump 136, according to an embodiment of the present disclosure. The pump 136 includes an inlet 900 and an outlet 902. A motor 904 is operable to pump fluid into the inlet 900 and out through the outlet 902.

Figure 9:
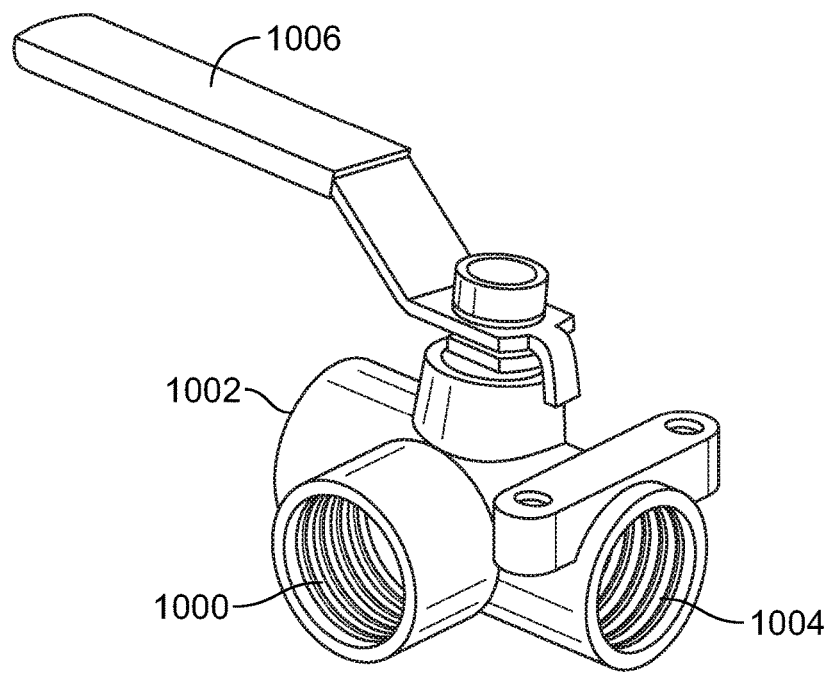
FIG. 9 illustrates a perspective lateral view of a valve, according to an embodiment of the present disclosure.

FIG. 9 illustrates a perspective lateral view of the valve 140, according to an embodiment of the present disclosure. The valve 140 may be a manual three way valve including an inlet 1000 in fluid communication with two branched outlets 1002 and 1004. A handle 1006 is moveably secured to the valve 140 and is coupled to a structure (such as ball or cylindrical wall having one or more fluid passages) that may be selectively moved between various positions in order to provide desired fluid flow through the valve 140. The handle 1006 may be engaged to move the valve 140 between fully closed and fully opened positions. The handle 1006 may be moved to positions less than fully closed and fully opened positions, in order to modulate fluid flow through the valve 140, thereby allowing for variable flow control.

Figure 10:
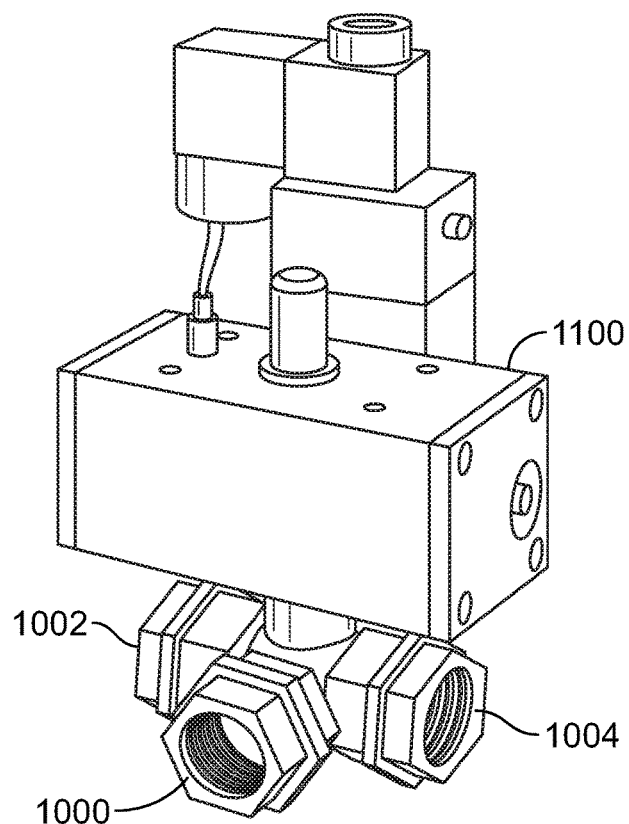
FIG. 10 illustrates a perspective lateral view of a valve, according to an embodiment of the present disclosure.

FIG. 10 illustrates a perspective lateral view of the valve 140, according to an embodiment of the present disclosure. The valve 140 is similar to that shown and described with respect to FIG. 9, except that the valve 140 shown in FIG. 11 may be a fully automatic valve. As such, the valve 140 may include an actuation system 1100 (such as a motor) that is configured to automatically control operation of the valve 140.

Figure 11:
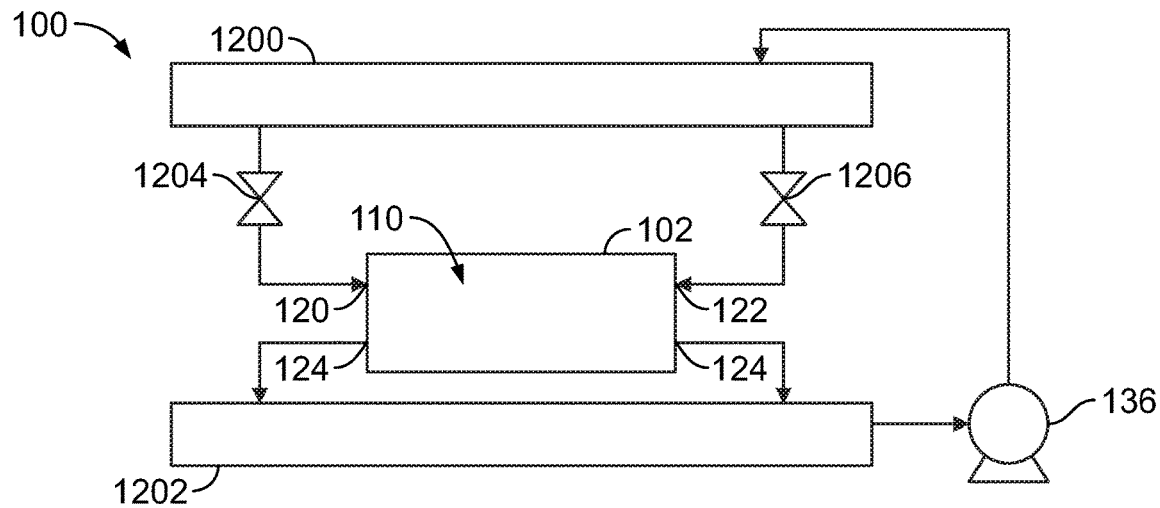
FIG. 11 illustrates a schematic diagram of a fluid testing system, according to an embodiment of the present disclosure.

FIG. 11 illustrates a schematic diagram of the fluid testing system 100, according to an embodiment of the present disclosure. In this embodiment, the component test chamber 102 is in fluid communication with an upper fluid reservoir 1200 and a lower fluid reservoir 1202. Test fluid within the upper fluid reservoir 1200 flows into the test chamber 110 from the fluid inlet ports 120 and 122 (when the valves 1204 and 1206 are open), and drains out of the test chamber 110 through fluid outlet ports 124 into the lower fluid reservoir 1202. The pump 136 operates to circulate the test fluid through the fluid testing system 100.

Figure 12:
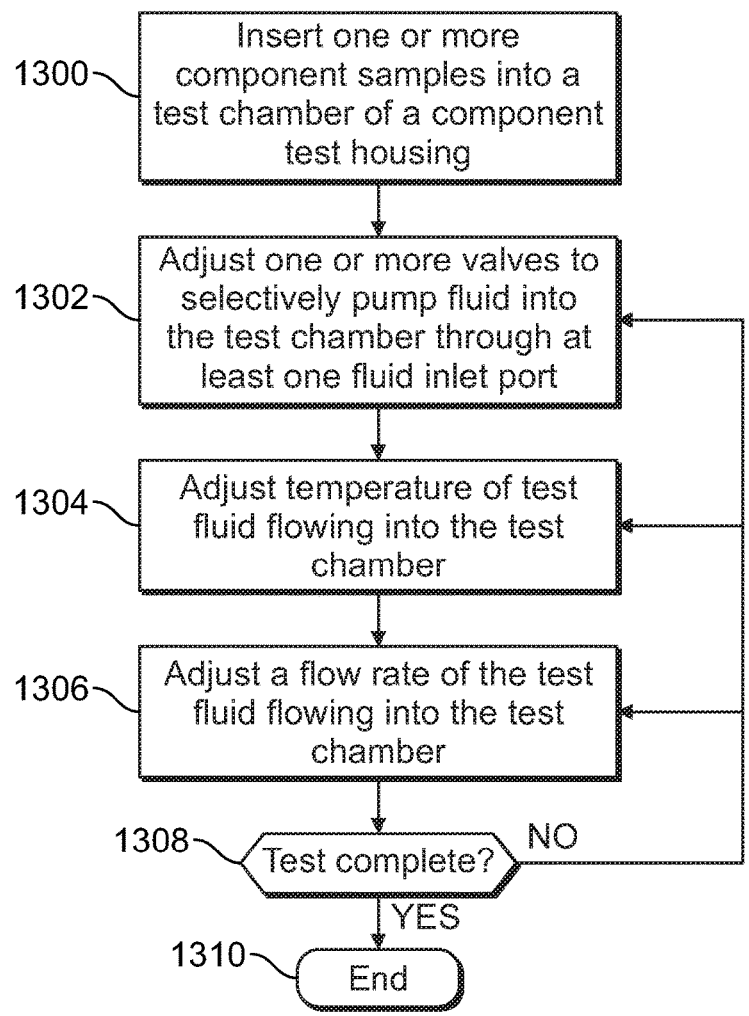
FIG. 12 illustrates a flow chart of a method of performing a fluid test with respect to one or more sample components, according to an embodiment of the present disclosure.

FIG. 12 illustrates a flow chart of a method of performing a fluid test with respect to one or more sample components, according to an embodiment of the present disclosure. The method begins at 1300, in which one or more component samples are inserted into a test chamber of a component test housing.

At 1302, one or more valves are adjusted to selectively pump test fluid into the test chamber through at least one fluid inlet port. At 1302, a temperature of the test fluid that flows into the test chamber is adjusted, such as through one or more temperature control devices. At 1306, a flow rate of the test fluid flowing into the test chamber is adjusted, such as through a variable speed pump. Steps 1302, 1304, and 1306 may occur concurrently. Optionally, any of steps 1302, 1304, or 1306 may occur before or after (and/or overlapping in time) with any of the other of the steps 1302, 1304, or 1306. Alternatively, the method may not include 1304 and/or 1306.

At 1308, it is determined whether the test is complete. If not, the method returns to any or all of steps 1302, 1304, and/or 1306. If, however, the test is complete, the method ends at 1310.

As described above, embodiments of the present disclosure provide fluid testing systems and methods that are configured to allow fluid to be pumped into a test chamber through multiple fluid inlet ports. In particular, the component test housing includes multiple fluid inlet ports that allow for fluid flow into the test chamber from multiple directions, which provides greater flexibility in configuring and executing a fluid test.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A fluid testing system comprising:
   a component test housing comprising a plurality of walls connected to a base and a cover, wherein a test chamber is defined between the plurality of walls, the base, and the cover, wherein the test chamber is configured to receive a sample component to be subjected to a fluid test;
   a plurality of fluid inlet ports formed through the component test housing, wherein the plurality of fluid inlet ports are configured to allow test fluid to flow into the test chamber from at least two different directions;
   a fluid flow rate sensor disposed within the test chamber, wherein the fluid flow rate sensor is configured to detect a velocity of the test fluid flowing within the test chamber;
   a pressure sensor disposed within the test chamber, wherein the pressure sensor is configured to detect a pressure within the test chamber; and
   at least one fluid reservoir in fluid communication with the test chamber.

2. The fluid testing system of claim 1, further comprising a test panel that is configured to retain the sample component.

3. The fluid testing system of claim 2, wherein the base comprises a recessed area, and wherein the test panel is removably secured to the recessed area.

4. The fluid testing system of claim 1, wherein each of the plurality of fluid inlet ports is coupled to the at least one fluid reservoir through one or more conduits.

5. The fluid testing system of claim 4, further comprising one or more valves disposed within the one or more conduits, wherein the one or more valves are configured to be selectively moved between open and closed positions to vary flow of the test fluid into the test chamber through the plurality of fluid inlet ports.

6. The fluid testing system of claim 4, further comprising at least one pump coupled to the one or more conduits, wherein the at least one pump is configured to circulate the test fluid between the test chamber and the at least one fluid reservoir.

7. The fluid testing system of claim 6, wherein the at least one pump is operated to variably control a flow rate of the test fluid into the test chamber.

8. The fluid testing system of claim 4, wherein the at least one fluid reservoir comprises at least two fluid reservoirs.

9. The fluid testing system of claim 8, wherein a first fluid reservoir retains a first test fluid of a first type, and a second fluid reservoir retains a second test fluid of a second type that differs from the first type.

10. The fluid testing system of claim 1, further comprising at least one temperature control device that is configured to control a temperature of the test fluid.

11. The fluid testing system of claim 1, wherein the component test housing is stationary during the fluid test.

12. The fluid testing system of claim 1, wherein the component test housing further comprises one or more fluid outlet ports in fluid communication with the at least one fluid reservoir, wherein the one or more fluid outlet ports are configured to drain the test fluid from the test chamber to the at least one fluid reservoir.

13. A fluid testing method comprising:
   receiving a sample component to be subjected to a fluid test within a test chamber of a component test housing that includes a plurality of walls connected to a base and a cover, wherein the test chamber is defined between the plurality of walls, the base, and the cover;
   selectively flowing test fluid into the test chamber from at least two different directions through a plurality of fluid inlet ports formed through the component test housing;
   detecting a velocity of the test fluid flowing within the test chamber by a fluid flow rate sensor that is disposed within the text chamber;
   detecting a pressure within the test chamber by a pressure sensor disposed within the test chamber; and
   coupling each of the plurality of fluid inlet ports to at least one fluid reservoir through one or more conduits.

14. The fluid testing method of claim 13, wherein the receiving comprises:
   retaining the sample component on a test panel; and
   removably securing the test panel within a recessed area formed in the base.

15. The fluid testing method of claim 13, further comprising:
  disposing one or more valves within the one or more conduits;
  selectively moving the one or more valves between open and closed positions; and
  varying flow of the test fluid into the test chamber through the plurality of fluid inlet ports via the selectively moving.

16. The fluid testing method of claim 13, further comprising:
  using at least one pump to circulate the test fluid between the test chamber and the at least one fluid reservoir;
  operating the at least one pump to variably control a flow rate of the test fluid into the test chamber; and
  controlling a temperature of the test fluid with at least one temperature control device.

17. The fluid testing method of claim 13, further comprising maintaining the component test housing in a stationary position during the fluid test.

18. The fluid testing method of claim 13, further comprising draining test fluid into the at least one fluid reservoir through one or more fluid outlet ports formed in the test housing.

19. A fluid testing system comprising:
  a test panel that is configured to retain a sample component;
  a component test housing comprising a plurality of walls connected to a base and a cover, wherein the base comprises a recessed area, wherein a test chamber is defined between the plurality of walls, the base, and the cover, and wherein the test panel is removably secured to the recessed area;
  a plurality of fluid inlet ports formed through the component test housing, wherein the plurality of fluid inlet ports are configured to allow test fluid to flow into the test chamber from at least two different directions;
  at least one fluid reservoir in fluid communication with the test chamber, wherein each of the plurality of fluid inlet ports is coupled to the at least one fluid reservoir through one or more conduits;
  one or more valves disposed within the one or more conduits, wherein the one or more valves are configured to be selectively moved between open and closed positions to vary flow of the test fluid into the test chamber through the plurality of fluid inlet ports;
  at least one pump coupled to the one or more conduits, wherein the at least one pump is configured to circulate the test fluid between the test chamber and the at least one fluid reservoir, wherein the at least one pump is operated to variably control a flow rate of the test fluid into the test chamber;
  at least one temperature control device that is configured to control a temperature of the test fluid;
  a temperature sensor disposed within the test chamber, wherein the temperature sensor is configured to detect a temperature within the test chamber;
  a fluid flow rate sensor disposed within the test chamber, wherein the fluid flow rate sensor is configured to detect a velocity of the test fluid flowing within the test chamber; and
  a pressure sensor disposed within the test chamber, wherein the pressure sensor is configured to detect a pressure within the test chamber.

\* \* \* \* \*